(12) United States Patent
Lewis et al.

(10) Patent No.: US 7,743,505 B2
(45) Date of Patent: Jun. 29, 2010

(54) METHODS FOR MANUFACTURING ENDODONTIC INSTRUMENTS FROM POWDERED METALS

(75) Inventors: Paul Lewis, Midvale, UT (US); John Nielsen, Cottonwood Heights, UT (US)

(73) Assignee: Ultradent Products, Inc., South Jordan, UT (US)

( * ) Notice: Subject to any disclaimer, the term of this patent is extended or adjusted under 35 U.S.C. 154(b) by 1082 days.

(21) Appl. No.: 11/063,757

(22) Filed: Feb. 23, 2005

(65) Prior Publication Data

US 2006/0185170 A1    Aug. 24, 2006

(51) Int. Cl.
*B21F 43/00* (2006.01)
*B23P 13/00* (2006.01)

(52) U.S. Cl. .................... 29/896.11; 29/896.1; 29/882; 72/205

(58) Field of Classification Search ............ 29/896.11, 29/896.1, 882, 747, 527.1; 451/48, 222; 433/102; 72/205
See application file for complete search history.

(56) References Cited

U.S. PATENT DOCUMENTS

| | | | |
|---|---|---|---|
| 1,372,170 A | 3/1921 | Judd | |
| 2,173,218 A | 9/1939 | Zoppi | |
| 2,390,254 A | 12/1945 | Henkle | |
| 2,434,286 A | 1/1948 | Pfann | |
| 2,640,253 A | 6/1953 | Fink et al. | |
| 2,701,505 A | 2/1955 | Fink | |
| 2,712,775 A | 7/1955 | Wilt | |
| 2,724,918 A * | 11/1955 | Triman | 156/345.15 |
| 2,907,151 A | 10/1959 | Peterson | 51/281 |
| 3,055,241 A * | 9/1962 | Hedgecock et al. | 72/205 |
| 3,406,555 A | 10/1968 | Fuchs et al. | |
| 3,803,014 A | 4/1974 | Atkinson | |
| 3,823,514 A | 7/1974 | Tsuchiya | |
| 3,869,373 A | 3/1975 | Schacher et al. | |

(Continued)

FOREIGN PATENT DOCUMENTS

EP    0119714    9/1984

(Continued)

OTHER PUBLICATIONS

Office Action dated May 6, 2005 cited in related U.S. Appl. No. 10/436,938.

(Continued)

*Primary Examiner*—Rick K Chang
(74) *Attorney, Agent, or Firm*—Workman Nydegger (57) ABSTRACT

Endodontic instruments or intermediate products (e.g., blanks) used to form finished endodontic instruments having a desired cutting edge and/or taper are formed, at least in part, by molding a metal powder into a desired shape and then sintering the metal particles together. The metal powder is initially formed into a green molded part that is sintered to yield a solid metal part. The sintered metal part may optionally be further processed by additional steps, as needed, to yield a finished endodontic instrument. One additional process includes cold forming the sintered metal body to provide a cutting edge, remove cracks and microfissures, or otherwise modify the characteristics of an intermediate product or endodontic instrument. Other processes include chemical milling and mechanical milling, grinding or cutting to sharpen the cutting edge, form a taper, or otherwise modify the intermediate product or endodontic instrument in a desired manner.

20 Claims, 5 Drawing Sheets

U.S. PATENT DOCUMENTS

| | | | |
|---|---|---|---|
| 3,894,570 A | 7/1975 | Reynolds | |
| 3,905,156 A | 9/1975 | Vogelsanger | 51/46 |
| 3,911,713 A | 10/1975 | Vydrin et al. | 72/205 |
| 3,948,073 A | 4/1976 | Lovell | |
| 4,116,755 A | 9/1978 | Coggins et al. | |
| 4,587,202 A | 5/1986 | Borysko | |
| 4,604,884 A | 8/1986 | Matsutani | |
| 4,611,509 A | 9/1986 | Matsutani | 76/24 R |
| 4,934,934 A | 6/1990 | Arpaio, Jr. et al. | 433/102 |
| 5,028,228 A | 7/1991 | Ubukata et al. | 425/298 |
| 5,219,284 A | 6/1993 | Velvart et al. | |
| 5,382,319 A | 1/1995 | Tumminaro, Jr. | |
| 5,477,604 A | 12/1995 | Smith et al. | 29/558 |
| 5,527,332 A | 6/1996 | Clement | |
| 5,539,973 A | 7/1996 | Smith et al. | 29/558 |
| 5,616,255 A | 4/1997 | Tumminaro, Jr. | |
| 5,620,537 A | 4/1997 | Bampton | |
| 5,628,674 A | 5/1997 | Heath et al. | 451/48 |
| 5,637,089 A | 6/1997 | Abrams et al. | |
| 5,644,834 A | 7/1997 | Smith et al. | 29/557 |
| 5,653,590 A | 8/1997 | Heath et al. | 433/102 |
| 5,682,665 A * | 11/1997 | Svanberg | 29/458 |
| 5,714,115 A | 2/1998 | Speidel et al. | |
| 5,741,429 A | 4/1998 | Donadio, III et al. | |
| 5,762,497 A | 6/1998 | Heath | |
| 5,762,541 A | 6/1998 | Heath et al. | 451/48 |
| 5,762,811 A | 6/1998 | Munoz | |
| 5,782,145 A | 7/1998 | Metzger | |
| 5,807,106 A | 9/1998 | Heath | |
| 5,882,198 A | 3/1999 | Taylor et al. | |
| 5,928,144 A | 7/1999 | Real | |
| 5,941,760 A | 8/1999 | Heath et al. | |
| 5,984,679 A | 11/1999 | Farzin-Nia et al. | |
| 6,018,860 A | 2/2000 | Smith et al. | 29/558 |
| RE36,628 E | 3/2000 | Sagae et al. | |
| 6,086,773 A | 7/2000 | Dufresne et al. | |
| 6,126,521 A | 10/2000 | Shearer et al. | 451/48 |
| 6,149,742 A | 11/2000 | Carpenter et al. | |
| 6,174,165 B1 * | 1/2001 | Katsuumi et al. | 433/102 |
| 6,213,771 B1 | 4/2001 | Fischer | |
| 6,258,182 B1 | 7/2001 | Schetky et al. | |
| 6,287,210 B1 | 9/2001 | Janusz et al. | |
| 6,299,445 B1 | 10/2001 | Garman | |
| 6,315,558 B1 | 11/2001 | Farzin-Nia et al. | |
| 6,375,458 B1 | 4/2002 | Moorleghem et al. | |
| 6,399,215 B1 | 6/2002 | Zhu et al. | |
| 6,428,634 B1 | 8/2002 | Besselink et al. | 148/421 |
| 6,575,747 B1 | 6/2003 | Riitano et al. | |
| 6,581,430 B2 | 6/2003 | Wilson | |
| 6,702,579 B1 | 3/2004 | Hoppe et al. | |
| 6,729,026 B2 | 5/2004 | Garcia et al. | 29/882 |
| 6,793,838 B2 | 9/2004 | Hansen et al. | |
| 6,865,919 B2 | 3/2005 | Litwinski et al. | |
| 6,890,134 B1 | 5/2005 | Wagner et al. | |
| 7,077,755 B2 | 7/2006 | Keener et al. | |
| 7,083,687 B2 | 8/2006 | Tanaka et al. | |
| 7,094,055 B2 | 8/2006 | Senia et al. | |
| 7,207,111 B2 | 4/2007 | Aloise et al. | |
| 7,223,100 B2 | 5/2007 | Brock et al. | |
| 2002/0137008 A1 | 9/2002 | McSpadden et al. | 433/102 |
| 2002/0182565 A1 | 12/2002 | Senia et al. | 433/102 |
| 2003/0068597 A1 | 4/2003 | Garman | 433/102 |
| 2004/0099356 A1 | 5/2004 | Wu | |
| 2004/0121283 A1 | 6/2004 | Mason | 433/102 |
| 2004/0126734 A1 | 7/2004 | Senia et al. | 433/102 |
| 2004/0229188 A1 | 11/2004 | Lewis et al. | 433/102 |
| 2004/0241037 A1 | 12/2004 | Wu | |
| 2005/0069837 A1 | 3/2005 | Lewis et al. | 433/102 |
| 2005/0109158 A1 | 5/2005 | Keener | |
| 2006/0014480 A1 | 1/2006 | Aloise et al. | |
| 2006/0027046 A1 | 2/2006 | Kugelberg et al. | |
| 2006/0086440 A1 | 4/2006 | Boylan et al. | |
| 2006/0185169 A1 | 8/2006 | Lewis et al. | |
| 2006/0185170 A1 | 8/2006 | Lewis et al. | |

FOREIGN PATENT DOCUMENTS

| | | |
|---|---|---|
| EP | 1354566 | 10/2003 |
| JP | 2002144154 | 5/2002 |

OTHER PUBLICATIONS

Notice of Allowance dated Jul. 14, 2005 cited in related U.S. Appl. No. 10/436,938.

Office Action dated Oct. 22, 2007 cited in related U.S. Appl. No. 10/991,178.

Notice of Allowance dated Apr. 3, 2008 cited in related U.S. Appl. No. 10/991,178.

Notice of Allowance dated Sep. 20, 2007 cited in related U.S. Appl. No. 11/282,852.

Office Action dated Mar. 13, 2008 cited in related U.S. Appl. No. 11/063,354.

Office Action dated Aug. 12, 2008 cited in U.S. Appl. No. 11/063,354.

* cited by examiner

METHODS FOR MANUFACTURING ENDODONTIC INSTRUMENTS FROM POWDERED METALS

BACKGROUND OF THE INVENTION

1. The Field of the Invention

The present invention relates to the manufacture of endodontic instruments. More particularly, the invention relates to a metal powder sintering process and a cold forming process for manufacturing endodontic files.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material forming the nerve of the tooth that has become infected and, after careful preparation of the canal that contained the nerve material, refill the canal with an inert filling material, such as gutta percha, permitting a patient to retain the tooth.

To achieve a successful root canal restoration, the dental practitioner must carefully and, as completely as possible, remove the infected pulp material of the tooth to prevent continued or future infection of surrounding tissues. The removal process typically includes shaping the root canal so that it can be effectively and successfully filled and sealed with an inert material. Filling and sealing minimizes the possibility of further infection occurring within the cleaned and shaped root canal.

Cleaning and shaping the root canal in preparation of sealing and filling the root canal is achieved by the use of metal files. The metal files have cutting surfaces for removing tissue in the root canal. The cutting surfaces are typically formed by helical flutes formed in the file. One or more helical cutting surfaces may be provided, which may be axially spaced as desired.

Some existing endodontic instruments and manufacturing methods are described in U.S. Pat. No. 4,934,934, U.S. Pat. No. 5,653,590, and U.S. Pat. No. 5,762,541.

Since root canals are seldom straight, often having bends and twists, at least some endodontic files are advantageously flexible. Currently preferred materials of construction include stainless steel, and more recently, nickel-titanium (Ni—Ti) alloys. Such materials, especially Ni—Ti alloys, exhibit good flexibility, resilience and strength, and are not likely to fail during use. Flexibility and strength are important to avoid file breakage during the cleaning process.

Current methods of manufacturing metal endodontic files require time intensive and costly methods. For example, stainless steel endodontic files are typically machined to form a cutting edge and then twisted to make a flute along the file's axis.

Another existing method of manufacturing existing endodontic files uses a grinding technique to form a cutting edge. In the grinding operation, a metallic (typically a titanium alloy) rod is advanced past a rotating grinding wheel at a relatively slow feed rate. The depth of cut may be varied along the length of the rod to produce a tapered endodontic file having a helical flute. Such a method is disclosed in U.S. Pat. No. 5,762,541.

While current manufacturing methods are capable of producing endodontic files in a variety of different shapes and sizes using a variety of different metals, there is still a great need to reduce the costs of manufacturing endodontic files. Forming an endodontic file from raw materials is currently a significant expense in the endodontic manufacturing process.

One problem with current processes is the time it takes to form each piece. For example, forming a cutting edge by grinding a metal wire can take more than a minute for each piece and the grinding machine can cost hundreds of thousand of dollars.

Another problem with endodontic manufacturing processes is they fail to reduce or sometimes cause stress fractures or weaknesses in the metal of the file. Even minor imperfections in the metal of an endodontic file can be problematic. Endodontic files are very thin, thus small imperfections can cause the file to break during use. A broken file in a root canal is very difficult to remove and can cause damage to the root canal.

Therefore, what is needed is a manufacturing process that can reduce the cost of manufacturing endodontic files while maintaining or improving the strength of the endodontic file.

BRIEF SUMMARY OF THE INVENTION

The present invention involves improved methods for manufacturing endodontic instruments such as endodontic files. Such methods can be used to manufacture a wide variety of endodontic instruments but are especially useful in manufacturing endodontic files having a taper. The inventive methods involve shaping a metal powder material into a desired shape of an endodontic instrument or intermediate product and then sintering the shaped metal power to form a solid sintered metal part. The sintered metal part can be a finished endodontic instrument or it can be an intermediate product that is further processed to yield a final product.

According to one exemplary embodiment, a method of manufacturing an endodontic instrument or intermediate product includes: (1) providing a mold having a mold cavity that defines the shape of a desired endodontic instrument or intermediate product; (2) introducing a molding material comprising a metal powder into the mold cavity and forming a green molded part; and (3) sintering the green molded part to form a solid sintered metal part having the shape of a finished endodontic instrument or an intermediate product. The sintering process can be carried out within the mold, or the molded part can be removed from the mold and then sintered. The solid sintered metal part can be used as is, or it may be further processed using one or more finishing processes to yield a finished endodontic instrument.

Examples of additional finishing processes include, but are not limited to, cold working of the sintered metal part (e.g., to remove defects, form a taper and/or cutting edge, or otherwise alter the shape of the part), grinding or milling (e.g., to form a taper, and/or a cutting edge), and chemical milling (e.g., to form a taper and/or sharpening the cutting edge).

The molding material used in the disclosed methods generally includes one or more types of metal powder (e.g., steel, titanium or titanium alloys). The molding material may also include one or more binders (e.g., thermoplastic or curable materials). A binder may be desirable because it helps the molded piece retain its shape before and during the sintering process. According one embodiment, the molding material is selected so as to suitable for metal injection molding. In this embodiment, the metal powder and a binder are heated to form a flowable molding material. The molding material is then injected into the mold and hardened (e.g., by cooling or curing the binder to yield a hardened binder).

The methods according to the invention are particularly useful in manufacturing tapered endodontic files because the taper can be directly introduced during the molding process, thereby obviating the need for additional grinding or milling procedures typically used to form a taper. In one embodiment, a mold including a mold cavity corresponding to a tapered endodontic file can be provided. The mold cavity may also include features corresponding to a cutting edge. In one embodiment, the solid sintered metal part may simply function as a blank used to form finished endodontic instruments therefrom.

According to one embodiment, the sintered solid metal part is further worked by cold forming (e.g., to form a cutting edge of an endodontic file). In that embodiment, cold forming typically involves (a) providing at least one die comprising a negative impression that corresponds to at least a partially formed cutting edge of an endodontic instrument; and (b) cold forming the sintered metal part using the at least one die and sufficient force to form a cutting edge in the blank. Cold forming can be performed using any suitable technique, examples of which include cold rolling, flat rolling, radial forming, and cold drawing. The cold forming process may yield a desired cutting edge, or a partially formed cutting edge may be further shaped, refined or sharpened by grinding and/or milling (e.g., mechanical or chemical milling).

The cold forming die can be used to form any number of cutting edges and to form a cutting edge with any desired shape. In one embodiment, cold forming the blank with one or more dies produces a blank having a polygonal cross section. The apexes of the polygonal cross section yield at least partially formed cutting edges.

Additional manufacturing steps that can be included in various embodiments of the present invention include cutting, grinding, machining, chemical milling, electrochemical milling, laser micromachining, grit blasting and combinations of these. These additional processing techniques can be used in various embodiments of the invention to further sharpen the partially formed cutting edge, dull the tip of the endodontic instrument, and/or provide a taper along the endodontic instrument.

The present invention provides many advantages for manufacturing endodontic instruments over the methods of the prior art. Because the blank or endodontic instrument is molded, intricate features such as a taper or a cutting edge can be easily formed. The molding step can significantly reduce the cost of forming these features as compared to traditional manufacturing techniques such as grinding or machining. Even in the case where the endodontic instrument is only partially formed during the molding process, the additional manufacturing steps such as cold forming or chemical milling are often more cost effective than forming the endodontic files using traditional manufacturing processes.

Another significant advantage of using a molding and/or cold forming step in the manufacture of endodontic instruments is the improvement in the properties of the material. The methods of the present invention are able to produce an endodontic instrument that is superior to existing endodontic instruments because the molding and/or cold forming step hardens the material and/or removes imperfections such as micro cracks and fissures. The improved endodontic instruments of the present invention are less likely to fatigue and break off inside a root canal because of these improved material properties.

These and other benefits, advantages and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

A detailed description of the endodontic instruments and manufacturing methods of the present invention will now be provided, with specific reference to figures illustrating preferred embodiments of the invention. It will be appreciated that like structures will be provided with like reference designations. To provide context for interpreting the scope of the invention, certain terms used throughout the application will now be defined.

As used herein, the terms endodontic "instrument" and endodontic "instruments" refer to endodontic files and other instruments used in a root canal or other endodontic procedure.

As used herein, the terms "polygon" and "polygonal" refer to a shape that is closed and bounded by straight or curved sides. Non-limiting examples include a triangle, a square, a rectangle, a pentagon, a spherical triangle, or any other of various regular or irregular shapes.

As used herein, the terms "chemical milling," "stripping" and "etching" refer to a procedure whereby a material is worked or shaped by exposure to a chemical bath. While exposed to the chemical bath, the shaping occurs as layers of metal are "stripped" or "etched" off because of the chemical action of the bath.

I. Exemplary Endodontic Instruments

Figure 1:
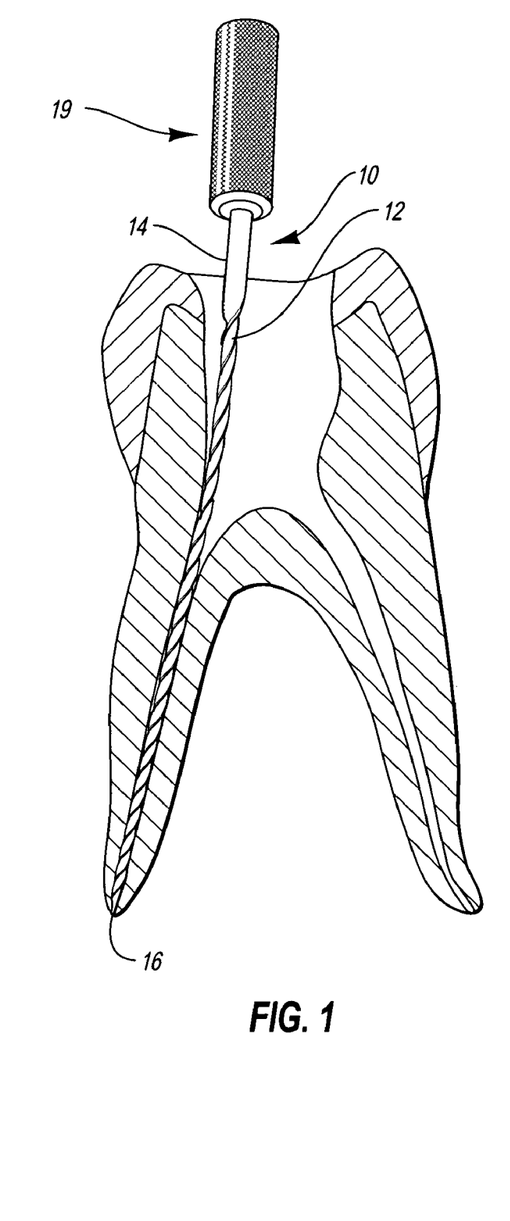
FIG. 1 is a cross sectional view of a tooth with an endodontic instrument positioned in one of two root canals.
Figure 2:
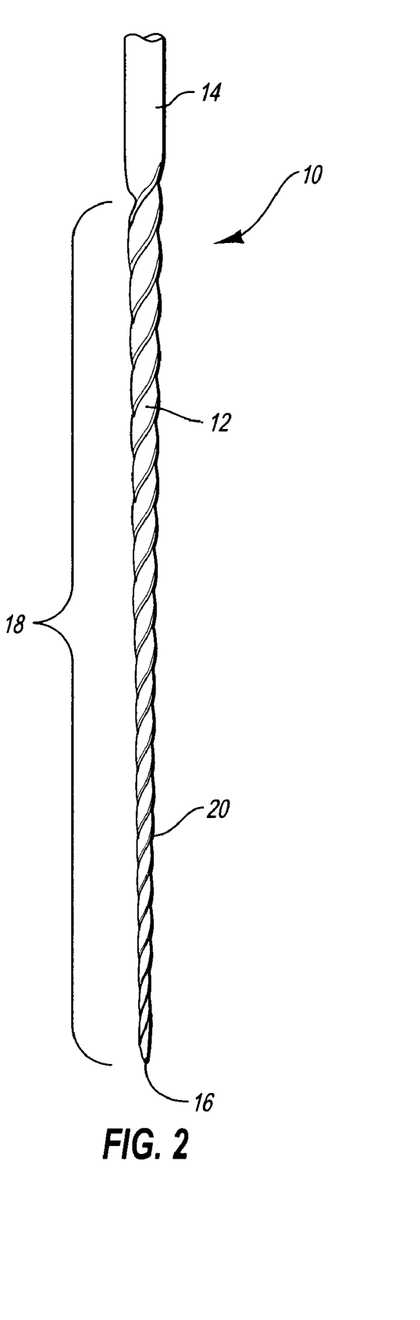
FIG. 2 is a perspective view of the cutting portion of an exemplary endodontic instrument.

Referring to FIGS. 1 and 2, an exemplary endodontic instrument 10 is illustrated which comprises a metallic rod 12 having a proximal end 14, and a distal end 16. At least a portion of the metallic rod 12 comprises a cutting portion 18, which is disposed between the proximal end 14 and the distal end 16. In this embodiment, the cutting portion 18 includes at least one helical cutting edge 20 that extends helically around metallic rod 12. A handle 19 is provided adjacent proximal end 14 of metallic rod 12 to facilitate gripping of the endodontic instrument 10 by a user or to provide attachment to dental tool (e.g., a rotating or reciprocating hand piece).

The cutting portion 18 is preferably tapered between the proximal end 14 and the distal end 16, with decreasing diameter or width toward the distal end 16. The taper can be continuous or incremental (i.e., stair-stepped). The taper can be any amount desired, but is preferably between about 0.02 mm/mm and about 0.06 mm/mm. The specific taper of any instrument depends on the intended use and dental practitioner preference. For example, a taper of 0.0225 mm/mm may be preferred when preparing a root canal that is to receive a gutta percha cone having a taper of about 0.02 mm/mm.

The cutting portion 18 may have a length of about 2 mm up to the full length of the rod 12, which may be as much as about 30 mm or more. In the illustrated embodiment, the cutting portion 18 has a length sufficient to extend substantially the full depth of a tooth root canal as illustrated in FIG. 1. It will be appreciated, however, that the cutting portion may terminate before reaching the distal end 16, as in a coronal file, or comprise a small length near distal end 16, as in an apical file. Terminating or reducing the length of the cutting portion 18 near distal end 16 creates a blunt tip that helps prevent undesirable penetration or edging of the instrument 10 into the root of the tooth or through the apex of the root.

Figure 3A:
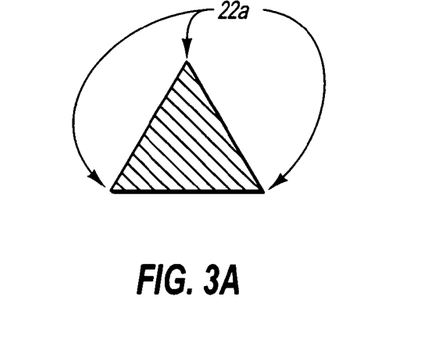
FIGS. 3A-3G illustrate different polygonal transverse cross sections of the cutting portion of several exemplary endodontic instruments manufactured according to the method of the present invention.

The cutting portion 18 of the instrument illustrated in FIGS. 1 and 2 has a cross-sectional configuration that is triangular and is composed of three linear sides, as best seen in FIG. 3A. The apices 22a of the triangle form cutting edges 20. In other embodiments, the cutting portion 18 may be of any polygonal cross-section such that when the rod is torsioned, helical cutting edges are formed.

Figure 3B:
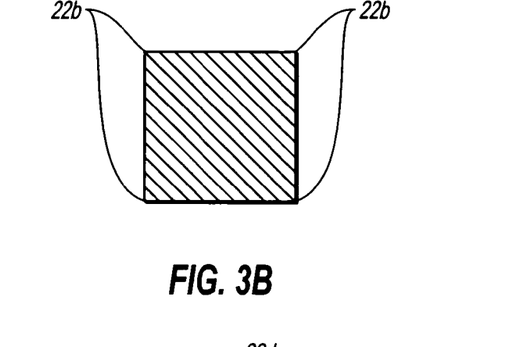
Figure 3C:
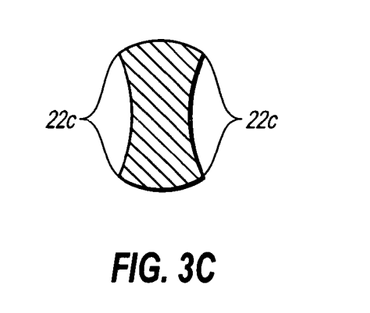

Several non-limiting examples of suitable polygonal cross-sections are illustrated in FIGS. 3A-3G. FIG. 3A illustrates a triangular cross section in which apices 22a form three cutting edges 20. FIG. 3B illustrates a square cross section in which line intersections 22b form four cutting edges. FIG. 3C illustrates a cross section bounded by four curved sides, two of which are concave and two of which are convex. The intersections 22c between the convex and concave sides form four cutting edges.

Figure 3D:
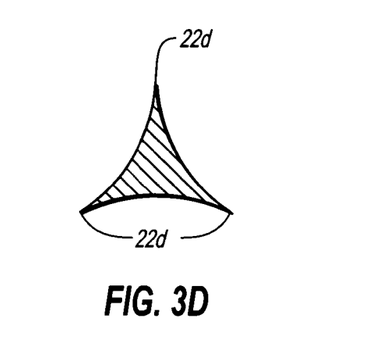
Figure 3E:
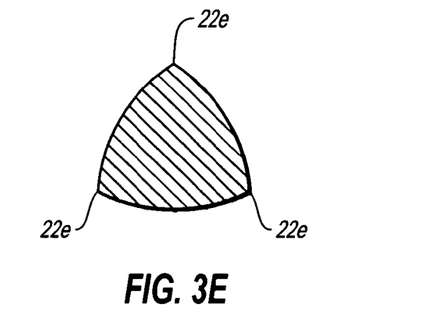

FIGS. 3D and 3E illustrate alternative spherical triangular cross sections, with the triangle cross section of FIG. 3D having concave surfaces between the apices 22d of the triangle and with the triangle cross section of FIG. 3E having convex surfaces between apices 22e of the triangle.

Figure 3F:
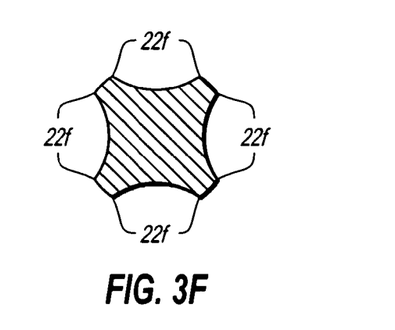
Figure 3G:
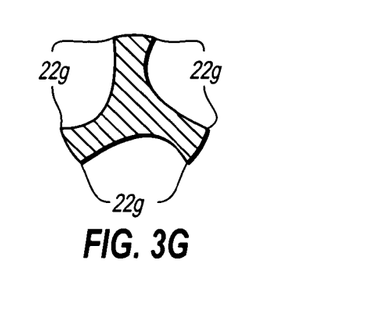

FIG. 3F illustrates a cross section bounded by a combination of four concavely curved sides separated by four straight sides. The intersection 22f between the straight and curved sides form eight cutting edges. FIG. 3G illustrates a cross section of an irregular polygon bounded by three concavely curved sides separated by three convexly curved sides. The intersections 22g between the six curved sides yield six cutting surfaces.

In an exemplary embodiment, the apices or edges 22a-22g of the various cross sections form helical cutting edges. In one embodiment, the helix is formed simultaneously with the formation of the cutting edge or the partially formed cutting edge. In an alternative embodiment twisting of the intermediate is used to form helical edges.

As described below, the endodontic instruments of the present invention are at least partially formed by performing a cold forming step. In an exemplary embodiment, during the cold forming step, the endodontic instrument is cold worked. This cold working improves the material properties of the endodontic file by removing some or all of the micro cracks and fissures (i.e., by reducing the number of dislocations in the crystal lattice of the metal in the blank). Since all larger cracks begin with micro cracks or fissures, the endodontic instruments of the present invention are less susceptible to cracking and breaking.

II. Methods of Manufacture

A. Forming A Powdered Metal Into an Endodontic Instrument or Intermediate Product In an exemplary embodiment of the invention, an endodontic instrument is manufactured using a metal powder as a starting material. The metal powder is molded to form a green mold part, which is then sintered to form a solid sintered metal part using a technique such as metal injection molding or other metal powder technique. Forming an instrument or blank using a metal powder facilitates the formation of various features of a blank or instrument, such as a taper and/or a cutting edge, which can be more difficult or expensive to form using other techniques such as grinding or machining.

In an exemplary embodiment, a method according to the present invention includes: (1) providing a mold having a mold cavity that defines an endodontic instrument or intermediate product; (2) introducing a molding material comprising a metal powder into the mold cavity and forming a green molded part; and (3) sintering the green molded part to form a solid sintered metal part having the shape of an endodontic instrument or intermediate product.

The mold includes a mold cavity shaped to form a part that has particular features of an endodontic instrument or intermediate product, such as a blank used to form an endodontic instrument. For example, the shape of the mold cavity can be configured to produce a part with a particular size, shape, taper, or cutting edge that corresponds to the size, shape, taper, or cutting edge of an endodontic instrument. In an exemplary embodiment, the mold cavity is configured to produce a part with a taper that is characteristic of an endodontic file.

Typically the mold has two halves that come together to form the mold cavity. Molds suitable for use with the present invention include molds similar to those used in plastic injection molding, including those with slides and multi-cavity configurations.

Because a molded part can shrink during sintering, the size of the mold cavity may be adjusted (e.g., increased) to accommodate for this shrinkage. The configuration of the molded part may also take into account changes that occur during other finishing steps, such as chemical milling. Those skilled in the art are familiar with using molds to produce intermediate parts that have correct dimensions for subsequent manufacturing steps.

The molding material includes at least one fine metal powder. Preferred metal powders include stainless steels and titanium based alloys. Stainless steel alloys are preferred for their relative inexpensive cost, good performance, and biological inertness. Titanium based alloys are typically preferred for their strength and flexibility.

Examples of suitable titanium based alloys include nickel titanium, nickel-titanium-chromium alloy, a nickel-titanium-copper alloy, a nickel-titanium-niobium alloy, or any other super-elastic metallic material. Although any suitable material can be used to make the endodontic instruments of the present invention, titanium-based alloys are preferred because they are strong, yet flexible and resilient. In one preferred embodiment, a nickel titanium alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients which do not adversely affect the suitability of the material for use as an endodontic instrument.

Another exemplary titanium-based alloy includes metal atoms selected from group IV and V transition metals and oxygen. Examples of such alloys include alloys having formulas of 1Ti—12Ta—9Nb—3V—6Zr—1O and 1Ti—23Nb—0.7Ta—2Zr—1O (mole percent). These titanium based alloys are also referred to as "gum metal." Additional details regarding these alloys are described in co-pending U.S. Provisional Application No. 60/586,738, filed Jul. 9, 2004, and entitled "Dental Abrading Instruments Made From Super-Elastic Alloys," which is incorporated herein by reference.

The molding material can include components in addition to the metal powders. Typically a binder is included in the molding material in order for the molded part to more easily retain its proper shape during handling and before sintering to form the solid metal part.

The components of the molding material depend in part on the particular powdered metal technique being used. In one embodiment, the powdered metal technique uses pressure and/or heat to form a molded part. In a preferred embodiment, the powdered metal technique is metal injection molding. For metal injection molding, the molding material includes a fine metal powder and a binder as discussed below. Those skilled in the art of powder metallurgy are familiar with the different types of materials and techniques that can be used in a molding and sintering process.

To form a metal part using metal injection molding, a molding material is used that includes a mixture of at least one fine metal powder and a binder. The binder is typically a wax or thermoplastic polymer. Those skilled in the art are familiar with the different types of binders that can be used with powdered metals. The molding material is usually a homogeneous mixture of about 60% volume metal powder and 40% volume binder, though other ratios are certainly within the scope of the invention.

In metal injection molding, the molding material is first heated until it is able to flow and is then injected into the mold cavity under relatively low pressure. The molding material is then allowed to cool, cure or otherwise solidify until it can be ejected as a molded part.

The molded part, or "green molded part," is then thermally processed. In one step the binder is removed by evaporation in an operation called debinding. Alternately, the molded part is immersed in a bath to dissolve a majority of the binder and then the part is exposed to ultraviolet light to harden the thermosetting component of the binder.

Once a green molded part is formed using metal injection molding or another metal powder molding process, the next step is to form a solid metal part. The solid metal part is formed by sintering the green molded part (i.e., heating the molded part to a temperature near the alloy melting point). Sintering temperatures are typically around 1200° C., but may vary depending on the particular metal or alloy being used. The shape of the molded part is preferably retained throughout this process, and close tolerances can be achieved.

One advantage of using the powdered metal technique of the present invention is that particular features such as a taper or cutting edge can be formed in a highly economical manner. For example, the metal injection molding process can be used to form a blank with the proper taper for an endodontic file. Forming a taper using traditional techniques such as grinding or machining can be time consuming and/or require expensive equipment. In contrast, forming a taper during the metal injection molding process, for example, only requires properly shaping the mold. The mold can then be used repeatedly to produce blanks and/or endodontic instruments with the proper taper.

An endodontic instrument formed using the powdered metal techniques of the present invention may or may not include a cutting edge. If the cutting edge is not part of the metal molding process, a cutting edge can be formed into the solid-metal part using the cold forming techniques discussed below. In this case, the solid-metal part (in this case a partially formed endodontic instrument) serves as a blank for the cold forming process. By forming the taper of the blank using a powdered metal technique, the taper does not need to be formed during the cold forming step, which means that less material has to flow during the cold forming step.

B. Cold Forming Methods

Exemplary methods of manufacturing endodontic instruments according to the present invention include forming at least a partially formed cutting edge in a partially formed endodontic instrument (i.e., a blank). The steps of an exemplary embodiment include (a) providing a blank comprising a deformable material; (b) providing at least one die comprising a negative impression that corresponds to at least a partially formed cutting edge of an endodontic instrument; and (c) cold forming the blank using the at least one die and sufficient force to form at least a partially formed cutting edge in the blank.

In an exemplary embodiment, the blank is formed using the metal powder and sintering technique described above. The cold forming technique is used to form a partially formed cutting edge in the solid-metal part, which is used as a blank in the cold forming process. Even where the sintered metal part includes a partially formed cutting edge, the solid metal part can be used as a blank in the cold forming process. In this embodiment, an endodontic instrument having a partially formed cutting edge is cold formed by properly aligning the partially formed cutting edge with the contours of a cold forming die. In this manner, the cold forming process can further define and/or sharpen the cutting edge.

In addition to forming a cutting edge, the methods of the present invention also include making various modifications to the cold-formed endodontic instrument. Exemplary modifications include forming a taper, making the tip of the endodontic instrument more blunt, and/or shaping the cutting edge to form a helix, such as by twisting the endodontic instrument.

1. Providing at Least One Die

The methods of the present invention utilize one or more dies to stamp, mold, or otherwise from a desired shape into the blank. The dies have a negative impression that a corresponds to a finished cutting edge or partially formed cutting edge of an endodontic instrument. The cutting edges illustrated in FIGS. 3A-3G, and discussed above, are examples of features to which the negative impression of the die can correspond. The negative impression can also correspond to other features of an endodontic instrument such as a blunt tip.

The negative impression can be completely formed in a single die or alternatively, the negative image can be spread across more than one die such that the use of the plurality of dies creates the proper corresponding cutting edge. The negative impression is also formed by accounting for the movement of the dies relative to the blank during the cold forming process. One advantage of using multiple dies is that the forces generated in the cold forming process can be spread across more than one die, thus reducing localized forces.

The negative impression can be formed into the die by grinding or etching the die or using other known techniques.

Those skilled in the art of cold forming are familiar with forming negative impressions that correspond to desired features to be formed in a cold forming process.

2. Cold Forming Step

The method of the present invention can include using at least one cold forming technique to form a finished cutting edge or a partially formed cutting edge. Various cold forming techniques can be used to form a cutting edge in the blank. Suitable cold forming techniques include roll forming, radial forming, flat rolling, cold drawing and similar techniques.

Figure 4A:
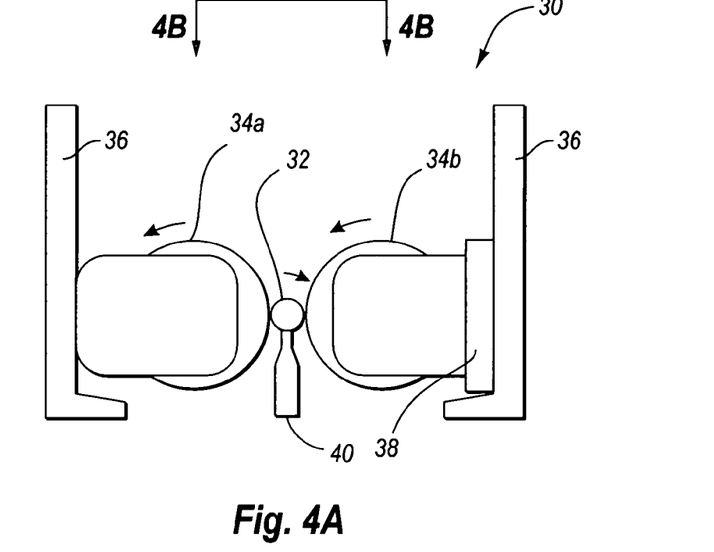
FIG. 4A is a schematic illustrating formation of a cutting edge of an endodontic instrument using a roll forming apparatus according to an exemplary embodiment of the present invention.

FIG. 4 schematically illustrates an exemplary apparatus 30 for roll forming a cutting edge in a blank 32. Roll forming apparatus 30 includes roll dies 34a and 34b. Roll dies 34a and 34b have a negative image of one or more desired features to be pressed into blank 32. Roll dies 34a and 34b are attached to a frame 36 and rotate about a horizontal axis. Roll die 34b can move relative to roll die 34a through the actuation of hydraulic press 38. A holder 40 positions the blank 32 between roll dies 34a and 34b. During the roll forming process, hydraulic press 38 forces roll dies 34a and 34b toward each other until the dies engage blank 32. Roll dies 34a and 34b are caused to rotate in the same direction, which causes blank 32 to rotate in an opposite direction. As roll dies 34a and 34b rotate, the negative image on dies 34a and 34b is pressed into blank 32.

Figure 4B:
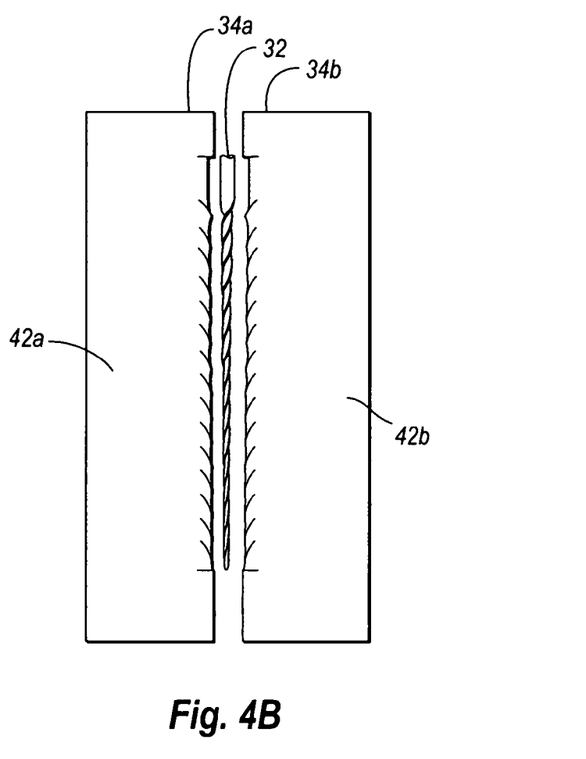
FIG. 4B is a top exploded view of the rollers and blank of FIG. 4A, where roll forming has been performed to form a cutting edge on the blank.

FIG. 4B shows an exploded perspective view of dies 34a and 34b engaging blank 32a. The surfaces 42a and 42b or dies 34a and 34b respectively show the negative impression of dies 34a and 34b. The negative impression corresponds to an at least partially formed cutting edge and a taper of an endodontic instrument. The rotation of dies 34a and 34b have formed an at least partially formed cutting edge and a taper in blank 32a.

In an exemplary embodiment, blank 32a is a solid-metal part formed using metal injection molding. Various techniques can be used to feed blank 32a into roll dies 34a and 34b.

Figure 5:
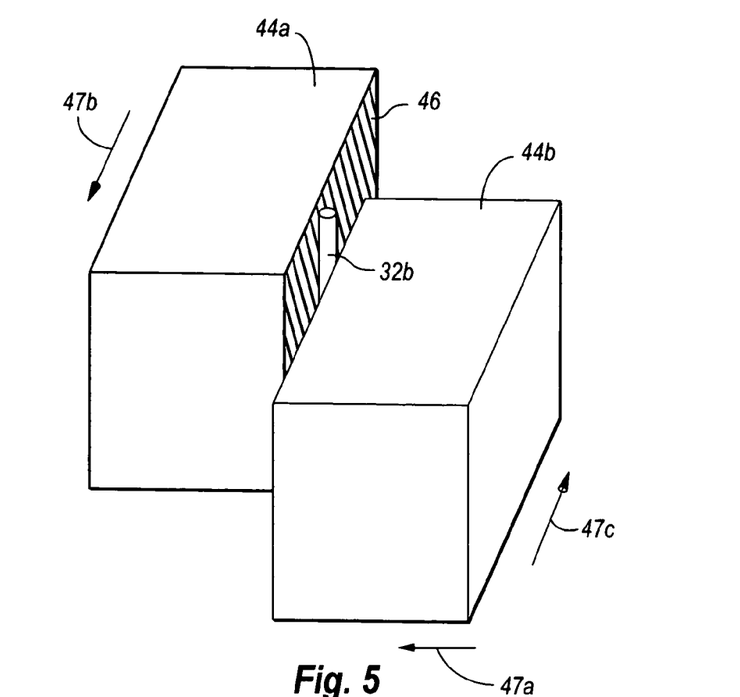
FIG. 5 is a schematic illustrating formation of a cutting edge of an endodontic instrument using a flat rolling apparatus according to an exemplary embodiment of the present invention.

In another embodiment of the invention, a blank is cold formed by flat rolling. FIG. 5 shows dies 44a and 44b that can be used in a flat rolling apparatus to form an endodontic instrument according to the present invention. In this embodiment, surface 46 of die 44a has a negative impression that corresponds to an at least partially formed cutting edge. The opposing surface of die 44b likewise has a negative impression that corresponds to an at least partially formed cutting edge.

Dies 44a and 44b are used to form an at least partially formed cutting edge in blank 32b by using a flat rolling apparatus, which presses dies 44a and 44b together to engage blank 32b as indicated by arrow 47a. Dies 42a and 42b are also caused to slide relative to one another as indicated by arrows 47b and 47c. As dies 44a and 44b slide relative to one another, blank 32b is rolled and the negative impression on the surfaces of dies 44a and 44b form an at least partially formed cutting edge.

Figure 6:
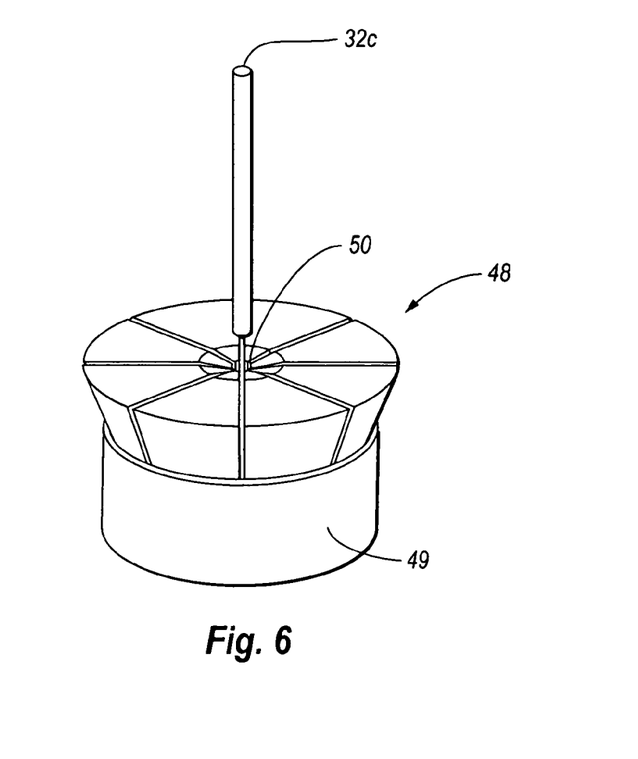
FIG. 6 is a schematic illustrating formation of a cutting edge of an endodontic instrument using a radial forming apparatus according to an exemplary embodiment of the present invention.

In yet another embodiment of the present invention, a radial forming process is used to form an endodontic instrument. FIG. 6 shows a set of radial dies 48 within an actuating ring 49. The set of radial dies 48 and actuating ring 49 are used in a radial forming apparatus generally known to those skilled in the art. The dies 48 have a negative impression on the surfaces that form cavity 50. The negative impression corresponds to an at least partially formed cutting edge and/or a taper of an endodontic instrument. These features are formed into blank 32c, positioned within dies 48, by forcing actuating ring 49 up around dies 48. As actuating ring 49 moves up, dies 48 are forced radially toward blank 32c. Dies 48 engage blank 32c and the negative impression on dies 46 forms an at least partially formed cutting edge in blank 32c.

In some embodiments of the present invention, two or more cold forming steps are performed to provide the desired feature or features. Those skilled in the art will be able (based on the present disclosure) to recognize the number and types of cold forming techniques that can be performed on a particular material.

Additional cold forming techniques can be used to form an at least partially formed cutting edge and/or other feature of an endodontic instrument according to the present invention. For example, other forms of rolling using non-symmetrical wheels or more than two wheels can be used. In addition, techniques such as extrusion and swagging can be used to form a cutting edge or a partially formed cutting edge.

The methods of forming an endodontic instrument using cold forming according to the present invention make it possible to form an endodontic instrument with almost any desired cross section. The endodontic instruments can have any desired taper and can have non-uniform features. Thus using the cold forming techniques of the present invention, the shape of the endodontic instrument can be selected to provide beneficial properties such as flexibility, in addition to desired cutting properties.

In some embodiments of the present invention, cold forming does not produce a finished product. For example, in some embodiments, cold forming does not produce a cutting edge that is sufficiently sharp or tapered. Whether a dental instrument is sufficiently sharp can depend on the preferences of the dental practitioner or the application that the instrument will be used in. Thus, in some embodiments of the present invention, additional steps or modifications, which are discussed below, may be needed. In these cases, the cold forming process produces an intermediate instrument. Nevertheless, even where cold forming only produces an intermediate instrument, the cold forming step or steps of the present invention can have many cost saving advantages by eliminating costly manufacturing processes, reducing the use of a costly manufacturing process, or by providing the opportunity to use an entirely new and cheaper process.

C. Additional Finishing Procedures

Additional steps can be performed to further modify the cold-formed blank to provide additional or enhanced features. For example, manufacturing the endodontic instruments can include forming a taper, sharpening the cutting edge, dulling the tip, forming a helical cutting edge, providing a grip or similar features.

Figure 7:
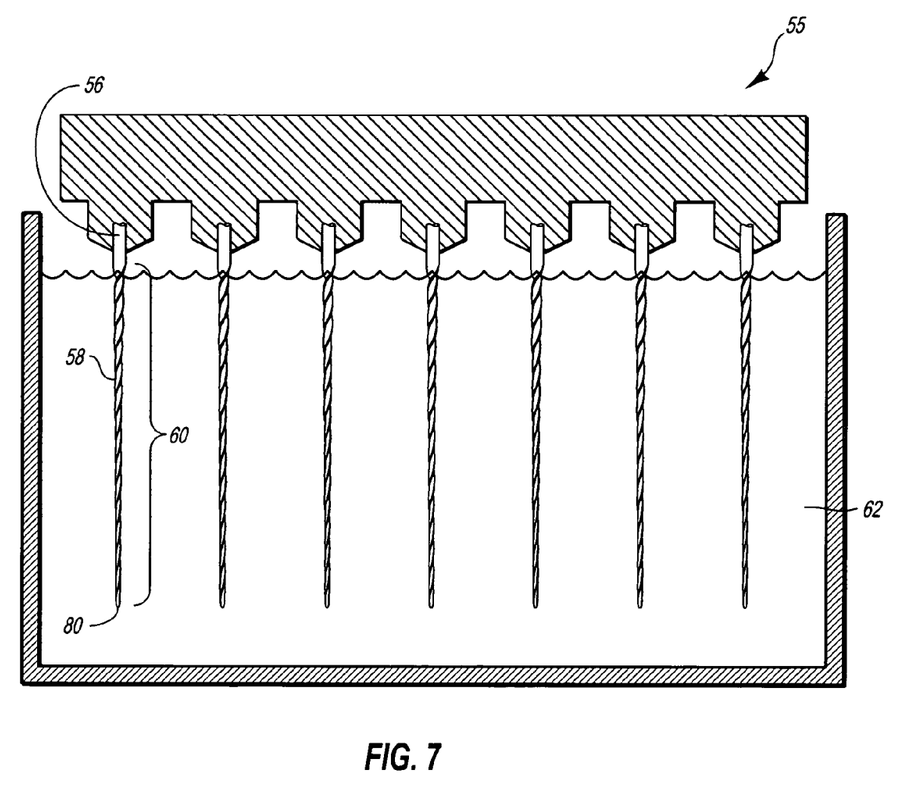
FIG. 7 is a schematic illustrating chemical milling of a plurality of endodontic instruments to sharpen the cutting edge of each of the plurality of endodontic instruments.

Various processes can be used to sharpen the cutting edge and/or form a taper. In an exemplary embodiment, a chemical milling process is used to sharpen the partially formed cutting edge, thereby producing a finished cutting edge. FIG. 7 shows an exemplary apparatus 55 for chemically milling an intermediate endodontic instrument 56 having a taper and partially formed cutting edge 58 along cutting portion 60. Any number of intermediate instruments can be simultaneously chemically milled as illustrated by the additional intermediate endodontic instruments illustrated in FIG. 7.

To chemically mill cutting edge 58 along portion 60, the intermediate endodontic instruments are submerged in chemical milling composition 62. In an exemplary embodiment, chemical milling composition includes an acid, water, and a wetting agent. Suitable acids include hydrofluoric acid and nitric acid. One currently preferred composition includes about 10% hydrofluoric acid, about 20% nitric acid, about 0.8% Dapco 6001, a wetting agent, and the balance water (% by volume).

In another embodiment, electrodes are connected to the chemical milling apparatus and the endodontic instruments such that a current passes through the chemical milling composition and the endodontic instrument. The current passing through the composition can heat the composition to increase the rate of the chemical milling reaction and/or to remove material from the surface of the intermediate endodontic file by electrolysis. For purposes of this invention, the use of chemical milling and electrolysis is referred to as electrochemical milling.

Chemically milling a partially formed cutting edge sharpens the edge because the chemical milling process removes an even layer of material from the surface. As material is evenly removed, the width of the cutting edge becomes progressively thinner, thus sharpening the cutting edge.

In another embodiment, intermediate instruments can also be tapered using a chemical milling process. The cutting portion 60 of each intermediate instrument is tapered by progressively inserting or withdrawing cutting portion 60 from chemical milling composition 62. The portions of the endodontic instrument that remain in chemical milling composition 62 for a longer period have more material removed. By withdrawing the endodontic instrument out of the chemical milling composition at a slow continuous rate, an even taper is formed.

In the case of instruments that are further processed by grinding or machining, chemical milling can be used to remove micro fissures or cracks caused by grinding that can easily propagate during use, causing fracture of the file in a person's root canal. Chemical milling can remove such cracks, yielding a superior contiguous surface and a file that is more resistant to breakage during use.

Additional aspects of chemical milling endodontic instruments is described in co-pending U.S. application Ser. No. 10/436,938, entitled "Methods of Manufacturing Endodontic Instruments," filed May 13, 2003, and co-pending U.S. application Ser. No. 10/991,178, entitled "Methods for Manufacturing Endodontic Instruments," filed Nov. 17, 2004, both of which are incorporated herein by reference.

Methods of manufacturing the endodontic instruments of the present invention can include the use of other known techniques such as cutting, grinding, machining, laser micromachining, grit blasting and combinations of these. A more detailed description of an exemplary machining or grinding process is set forth in U.S. Pat. No. 5,762,541, which is incorporated by reference with respect to machining or grinding, but which is modified and improved according to the invention so as to include the cold forming processes as disclosed herein. These techniques can be used to sharpen the cutting edge, create a taper, or otherwise modify the endodontic instrument. For example, some endodontic instruments are formed to have a somewhat dulled or blunt tip such that the tip of the endodontic instrument does not pierce through the walls of the root canal or cause ledging. Dulling the tip can be economically accomplished using a grinder.

In some exemplary embodiments, the forming methods disclosed herein yield an intermediate instrument that requires torsioning or twisting to form a helical cutting edge. Torsioning is typically accomplished by holding one end of the cutting portion stationary while twisting the opposite end. Torsioning an intermediate instrument can cause the apices of polygonally-shaped instrument to be twisted to form helical cutting surfaces along the cutting portion. Endodontic instruments typically have a helical cutting edge. Helical cutting edges are advantageous because they can cut or remove tissue as a practitioner turns the instrument in the root canal or moves the instrument up and down within the root canal.

The endodontic instruments and methods of manufacturing endodontic instruments, according to the present invention, provide many advantages over the instruments and methods of the prior art. Forming the cutting edge or partially forming the cutting edge using the processes described herein greatly reduces the time and expense for manufacturing endodontic instruments. In addition, cold forming the endodontic instruments improves the material properties of the instruments thereby reducing the likelihood of breakage during an endodontic procedure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing an endodontic instrument or an intermediate product, comprising:
    (a) providing a mold having a mold cavity that at least partially corresponds to or approximates a shape of an endodontic instrument or an intermediate product having a proximal end and a distal end, that is essentially straight between the proximal end and the distal end, and that has a length and a width so as to be readily insertable within a root canal of a tooth;
    (b) inserting a molding material comprising a metal powder into the mold cavity and shaping the molding material to form a green molded part that corresponds to or approximates the shape of an endodontic instrument or an intermediate product having a proximal end and distal end, that is essentially straight between the proximal end and the distal end, and that has a length and a width so as to be readily insertable within a root canal of a tooth;
    (c) sintering the green molded part to form a solid metal part having a shape that at least partially corresponds to or approximates the shape of an essentially straight endodontic instrument or an intermediate product having a length and a width so as to be readily insertable within a root canal of a tooth; and
    (d) cold working the solid metal part in order to harden and/or remove imperfections in the solid metal part,
    the method yielding an endodontic instrument or an intermediate product including an at least partially formed cutting edge in the solid metal part.

2. A method as in claim 1, wherein the molding material used to form the green molded part further comprises a binder mixed with the metal powder.

3. A method as in claim 2, wherein the green molded part is formed by injection molding the molding material.

4. A method as in claim 1, wherein the metal powder comprises a metal selected from the group comprising steel, stainless steel, nickel-titanium alloy, gum metal, and combinations thereof.

5. A method as in claim 1, wherein the mold cavity and the sintered metal part both include a taper characteristic of an endodontic file.

6. A method as in claim 1, wherein cold working the sintered metal part increases a strength and/or decreases a modulus of elasticity of the solid-metal part.

7. A method as in claim 1, wherein (d) yields an endodontic instrument or an intermediate product having helical cutting edges.

8. A method as in claim 1, wherein (b) yields an endodontic instrument or an intermediate product having helical cutting edges.

9. A method as in claim 1, wherein (d) is performed by at least one cold forming process selected from the group consisting of roll forming, radial forming, flat rolling, and cold drawing.

10. A method as in claim 1, further comprising sharpening the at least partially formed cutting edge by chemical milling.

11. A method as in claim 1, the method yielding an endodontic instrument or an intermediate product including a taper and at least three cutting edges spaced around a longitudinal axis of the endodontic instrument or the intermediate product.

12. A method of manufacturing an endodontic instrument or an intermediate product, comprising:
   (a) providing a mold having a mold cavity that at least partially corresponds to or approximates a shape of an endodontic file or an intermediate product having a proximal end and a distal end, that is essentially straight between the proximal end and the distal end, that has a taper extending along a length between the proximal end and the distal end, that includes an at least partially formed cutting edge, and that has a length and a width so as to be readily insertable within a root canal of a tooth;
   (b) inserting a molding material comprising a metal powder into the mold cavity and shaping the molding material to form a green molded part having a proximal end and a distal end, that is essentially straight between the proximal end and the distal end, that has a taper extending along a length between the proximal end and the distal end, that includes an at least partially formed cutting edge, and that has a length and a width so as to be readily insertable within a root canal of a tooth; and
   (c) sintering the green molded part to form a solid metal part.

13. A method as in claim 12, further comprising cold working the solid metal part to further modify and/or sharpen the at least partially formed cutting edge.

14. A method as in claim 12, further comprising chemical milling the solid metal part to sharpen the at least partially formed cutting edge.

15. A method as in claim 12, the method yielding an endodontic instrument or an intermediate product including a taper and at least three cutting edges spaced around a longitudinal axis of the endodontic instrument or the intermediate product.

16. A method of manufacturing an endodontic instrument or an intermediate product, comprising:
   (a) providing a mold having a mold cavity that at least partially corresponds to or approximates a shape of an endodontic file or an intermediate product having a proximal end and a distal end, that is essentially straight between the proximal end and the distal end, that has a taper extending along a length between the proximal end and the distal end, that includes an at least partially formed cutting edge, and that has a length and a width so as to be readily insertable within a root canal of a tooth;
   (b) inserting a molding material comprising a metal powder and a binder into the mold cavity and shaping the molding material to form a green molded part having a proximal end and a distal end, that is essentially straight between the proximal end and the distal end, that has a taper extending along a length between the proximal end and the distal end, that includes an at least partially formed cutting edge, and that has a length and a width so as to be readily insertable within a root canal of a tooth;
   (c) causing or allowing the binder to at least partially harden;
   (d) sintering the green molded part to form a solid metal part; and
   (e) cold working the solid metal part to modify the at least partially formed cutting edge.

17. A method as in claim 16, further comprising sharpening the at least partially formed cutting edge by chemical milling.

18. A method as in claim 16, further comprising modifying the at least partially formed cutting edge by at least one of mechanical cutting, milling or grinding.

19. A method as in claim 16, further comprising forming a helical cutting edge into the endodontic instrument or the intermediate product.

20. A method as in claim 16, the method yielding an endodontic instrument or an intermediate product including a taper and at least three cutting edges spaced around a longitudinal axis of the endodontic instrument or the intermediate product.

* * * * *

UNITED STATES PATENT AND TRADEMARK OFFICE
CERTIFICATE OF CORRECTION

PATENT NO.        : 7,743,505 B2
APPLICATION NO.   : 11/063757
DATED             : June 29, 2010
INVENTOR(S)       : Lewis et al.

It is certified that error appears in the above-identified patent and that said Letters Patent is hereby corrected as shown below:

Column 2
Line 58, change "as to suitable" to --as to be suitable--

Column 5
Line 4, after "provide attachment to" insert --a--
Line 28, change "instrument" to --instrument 10--
Line 51, change "intersection 22f" to --intersections 22f--

Column 6
Line 59, before "nickel-titanium-chromium alloy" insert --a--

Column 8
Line 49, change "from" to --form--
Line 50, after "that" remove [a]

Column 9
Line 11, change "FIG. 4" to --FIG. 4A--

Column 10
Line 1, change "dies 46" to --dies 48--
Line 62, before "chemical milling composition" insert --the--

Column 11
Line 61, after "apices of" insert --a--

Signed and Sealed this

Fourteenth Day of December, 2010

David J. Kappos
*Director of the United States Patent and Trademark Office*